United States Patent [19]

de Graaf et al.

[11] 4,383,124
[45] May 10, 1983

[54] METHOD FOR THE PREPARATION OF ALDEHYDES

[75] Inventors: Theodorus F. M. de Graaf, Beek; Hubertus J. A. Delahaye, Voerendaal, both of Netherlands

[73] Assignee: Stamicarbon, B.V., Geleen, Netherlands

[21] Appl. No.: 248,438

[22] Filed: Mar. 27, 1981

[30] Foreign Application Priority Data

Mar. 29, 1980 [NL] Netherlands .......................... 8001878

[51] Int. Cl.³ .............................................. C07C 45/51
[52] U.S. Cl. ..................................... 568/485; 568/487
[58] Field of Search ................ 568/485, 486, 487, 488

[56] References Cited

U.S. PATENT DOCUMENTS 3,558,716  1/1971  Engelhardt .......................... 568/485

FOREIGN PATENT DOCUMENTS 1444484  7/1976  United Kingdom ................ 568/485

*Primary Examiner*—Werren B. Lone

[57] ABSTRACT

An improved process for the dehydrogenation of alcohols, to produce aldehydes therefrom, using a copper-containing catalyst, is described wherein the alcohol is introduced in the gas phase initially in admixture with an inert gas only, and after an initial reaction period the alcohol is continued to be introduced, in the gas phase, in an admixture with an inert gas together with a minor amount of hydrogen. As a result, prolonged catalyst activity with retained selectivity is achieved.

9 Claims, No Drawings

METHOD FOR THE PREPARATION OF ALDEHYDES

The invention relates to a method for the preparation of aldehydes by the dehydrogenation of monovalent primary alcohols.

In British patent specification No. 1,444,484 a method is described for the dehydrogenation of alcohols in the gas phase by means of a copper-containing catalyst. In that process, the dehydrogenation is effected in the presence of water vapor and small quantities of an inert gas in order to obtain a catalyst with a long useful service life, a very good selectivity and a high conversion.

The result of the use of water vapor in such a dehydrogenation process is that, in the upgrading of the gaseous reaction mixture obtained, by condensation and separating the condensate by distillation, problems will often arise because of the formation of an azeotrope, with water, of the reaction product to be recovered and possibly of the starting product present. While it is true that such an azeotropic mixture can be recirculated, in many cases that means a substantial recirculation of the desired product.

In applying the method according to the said British patent specification for the dehydrogenation of monovalent primary alcohols, the length of life of the catalyst and of the selectivity of the conversion of alcohols into aldehydes are, moreover, less than satisfactory.

A method has now been found for the dehydrogenation of monovalent primary alcohols, in which process no water vapor need be added to the starting product, and using relatively large amounts of an inert gas, and a very long length of life for the catalyst, as well as a high degree of selectivity, can be achieved.

The method according to this invention for the preparation of aldehydes by dehydrogenation, using a copper-containing catalyst, of monovalent primary alcohols in the gas phase is characterized in that the dehydrogenation is initially effected in the presence of an inert gas for an initial period of time and then subsequently use of the same catalyst is continued for a subsequent extended period of time while effecting the dehydrogenation of the alcohol in the presence of a mixture of an inert gas and hydrogen. The gas mixtures are substantially dry, i.e., substantially free from water vapor so that the above-described azeotropic formation is avoided.

The method according to this invention is applied with various monovalent primary alcohols, both aliphatic and aryl-aliphatic, which can be used as starting material, particularly monovalent primary alcohols with from 2 to 20 carbon atoms such as, for instance, ethanol, octanol-1, decanol-1, dodecanol-1, 2-hexanol-1, undec-10-enol-1, 2-methylundecanol-1, phenylethanol and cinnamic alcohol.

The use of nitrogen (being the most available and least expensive) is preferred as the inert gas, but other inert gases as well can in principle be used. The amount of inert gas (separately and later in the mixture with hydrogen) may vary within wide limits, for instance, from 2 to 100 moles of inert gas per mole of the gas phase alcohol introduced. A very suitable result can be achieved in applying from about 5 to about 40 moles of inert gas per mole of alcohol introduced. The quantity of hydrogen used in the second extended period may also vary within wide limits, for instance, from 0.5 to 50 moles of hydrogen per mole of alcohol introduced. Preferably, from about 1 to 20 moles of hydrogen are used per mole of alcohol introduced. The molar ratio of nitrogen to hydrogen should, however, be greater than 0.5:1 preferably from about 1:1 up to 20:1.

The initial period for the dehydrogenation process using only an inert gas with the gas phase alcohol is governed by the time when the catalyst has reached the desired level of selectivity, which can generally be realized within from 2 to 24 hours at which time this initial period of the process is terminated. Then, by the on-going use of a mixture of inert gas and hydrogen, that desired level of selectivity of the catalyst can be maintained for a long time, for instance, even some months.

In applying the method according to the invention, copper-containing dehydrogenation catalysts, which are already known per se are used; the catalyst formation itself is not part of this invention. These include copper carried by a carrier such as, for instance, magnesium oxide, zinc oxide, chromic oxide, aluminum oxide, silicon oxide, or a mixture of two or more of the said oxides. If desired, oxides of alkali metals and/or earth alkali metals can also be added to the catalyst composition as promotor.

Temperatures of from 200° to 450° C. are generally suitable for the purpose of effecting the dehydrogenation according to this invention. Preferably, a temperature of from about 225° to 350° C. is used. By allowing only a very gradual increase of the temperature, for instance a temperature increase corresponding to as little as an average of one degree Centigrade in three days, the activity of the catalyst can be kept constant for a long time. Such gradual temperature increase in the practice of this invention desirably may range from, on the average, as little as 0.25° rise/day up to about 3°/day.

The space velocity for the dehydrogenation process is generally controlled to be between 0.05 and 10 kg alcohol per liter of catalyst (bulk volume). A higher space velocity can be in principle also be employed, but this does not result in any advantage.

The gaseous reaction mixture obtained from applying the method of this invention can be separated, by cooling, into a condensate, containing the desired product, and a gas mixture, which can then be recirculated, if desired. If this gas mixture is recirculated, the quantity of hydrogen formed must, however, be removed in view of the formation of hydrogen in the dehydrogenation process. The condensate obtained in said cooling process can be separated by distillation into the aldehyde formed and, possibly, non-converted alcohol, which can then be re-used.

The aldehydes obtained by applying the method according to the invention are useful as raw material for the preparation of various valuable products, inter alia, perfumes.

In the following Examples, the invention is further elucidated, without being limited to the specific embodiments illustrated.

EXAMPLE I

Through a vertical glass tube-shaped reactor (internal diameter 25 mm, height 40 cm), filled with 25 ml of catalyst granules (Cu on MgO, 45% weight of Cu, diameter and length of the granules 3 and 5 mm respectively), a gaseous mixture of octanol-1 (16.5 g per hour) and nitrogen (20 moles per mole octanol) is passed downwardly over the catalyst at atmospheric pressure for 10 hours. By means of jacket heating, the temperature in the reactor (measured about 1 mm above the catalyst) is kept at 265° C. Thereafter, for a period of 4 weeks, a gaseous mixture of hydrogen, nitrogen and octanol-1 (16.5 g octanol per hour, 1 mole hydrogen and 9 moles nitrogen per mole octanol) is passed over the catalyst with only a very gradual increase in temperature (at the end of said period the temperature is 329° C.). The gaseous reaction mixture thus obtained is removed via a receiving tank cooled to 12° C. The condensate formed in the receiving tank is periodically analyzed gaschromatographically. This analysis shows that, 4 days after commencement of the passing over of hydrogen-containing gas mixture, the selectivity is 99% and the octanol conversion 58%. During the rest of the experiment, the selectivity and the conversion contined to be 99 and 58% respectively.

The catalyst used in this Example is prepared as is known in the art by precipitation from a solution containing copper and magnesium salt, followed by filtration, drying, granulation and reduction of the granules in the reactor with a hydrogen-nitrogen mixture at a temperature of 265° C.

EXAMPLE II

Example I was repeated, using, however, a different molar ratio hydrogen:nitrogen;octanol, viz., 2.5:7.5:1. Four days after commencement of the introduction of hydrogen-containing gas mixture the selectivity is 99% and the conversion 45%. After 12 weeks, the experiment was concluded (at the end of this period the temperature was 313° C.) without experiencing any decrease in these selectivity and conversion limits.

EXAMPLE III

Example II was repeated, however, with initial application of a temperature of 275° C. (instead of the temperature of 265° C. as mentioned in Example I). The experiment was ended after 6 weeks (at the end of this period the temperature was 317° C.). The selectivity is 99% and the conversion 55%.

COMPARATIVE EXAMPLE A

Example II is repeated, except that the use of an initial period (as described in Example I) with a flow of the octanol/nitrogen mixture for 10 hours was omitted. During an experiment of 6 weeks duration (at the end of this period the temperature is 290° C.) the selectivity is only 30%. The conversion is 75%. Such a low selectivity is unacceptable in practice.

COMPARATIVE EXAMPLE B

Example I is repeated, however, except that during the extended period of the process, 10 moles nitrogen only per mole octanol are now used instead of 1 mole hydrogen and 9 moles nitrogen. It is found that the conversion now shows a rapid decline, viz., of about 10% a day (by increasing the temperature, this decline cannot be avoided while maintaining a proper selectivity), so that the experiment has to be ended after a few days.

COMPARATIVE EXAMPLE C

Example I is repeated. But, instead of the flow of 1 mole hydrogen and 9 moles nitrogen, 5 moles hydrogen only per mole octanol are now used. Instead of a temperature of 265° C. as in Example I, a temperature of 305° C. has to be applied in order to reach a good conversion level (50%). It is found that a good conversion with a proper selectivity could be maintained for only a short time of a few days.

EXAMPLE IV

Example I was repeated with decanol-1. First a nitrogen/decanol mixture (20 moles nitrogen per mole decanol, 16.6 g decanol per hour) was passed, for 10 hours, over the catalyst and at a temperature of 265° C., then subsequently a stream of hydrogen (2.5 moles hydrogen and 7.5 moles nitrogen per mole decanol) as well. The receiving tank was cooled at 30° C. After the hydrogen/nitrogen/decanol mixture had been passed over for about 4 days, a selectivity of 99% was reached, with a conversion of 40%. These levels were then maintained during the balance of the experiment, which lasts 6 weeks (at the end of the experiment the temperature was 289° C.).

EXAMPLE V

Example IV was repeated, employing, however, a temperature of 275° C. (instead of 265° C.). After the hydrogen-containing mixture had been passed over the catalyst for about 4 days, the selectivity was 99% and the conversion 50%, which values were then maintained during the 6 weeks duration of the experiment (temperature at the end of the experiment 317° C.).

It will thus be seen that by avoiding the presence of water vapor, and by using relatively large amounts of an inert gas, and by using for an initial reaction period a mixture of the alcohol vapors with such inert gas only, and then using, for an extended second reaction period a mixture of the inert gas with a minor amount (relative thereto) of hydrogen, a much improved process and catalyst performance is achieved.

What is claimed is:

1. In processes for the preparation of aldehydes by dehydrogenation of monovalent primary alcohols, having from 2 to 20 carbon atoms, in the gas phase by means of a copper-containing catalyst, the improvement consisting essentially in effecting said dehydrogenation during an initial reaction period using a gas phase mixture of an inert gas and said alcohol and thereafter effecting subsequent dehydrogenation for a second extended reaction period of time using a mixture of said alcohol with an inert gas together with hydrogen.

2. Process according to claim 1, wherein from 5 to 40 moles of inert gas are used per mole alcohol introduced.

3. Process according to claims 1 or 2, wherein from 1 to 20 moles of hydrogen are used per mole alcohol introduced during said second reaction period.

4. Process according to claims 1 or 2, wherein the dehydrogenation is effected over a temperature range of from about 225° to 350° C.

5. Process according to claims 1 or 2, wherein during the second reaction period of the dehydrogenation process, in the presence of the mixture of inert gas and of hydrogen, the temperature is controlled so as to increase only very gradually.

6. Process according to claims 1 or 2, wherein said gas phase is free from water vapor during both said initial reaction period and said second extended reaction period.

7. Process according to claims 1 or 2, wherein during said second reaction period the molar ratio of nitrogen:hydrogen is greater than about 0.5:1.

8. Process according to claims 1 or 2, wherein during said second reaction period, said temperature increase is, on the average, from about 0.25° up to about 3° per day.

9. Process according to claim 1, wherein said inert gas is nitrogen.

* * * * *